(12) United States Patent
Itchoda et al.

(10) Patent No.: US 10,836,996 B2
(45) Date of Patent: Nov. 17, 2020

(54) CELL CULTURE KIT, SCREENING METHOD, AND METHOD OF MANUFACTURING CELL CULTURE KIT

(71) Applicants: Corning Incorporated, Corning, NY (US); Public University Corporation Yokohama City University, Yokohama-shi (JP)

(72) Inventors: Yoko Itchoda, Tsukuba (JP); Go Tazaki; Motohiro Fukuda, Tsukuba (JP); Hitoshi Tsuruta, Tsukuba (JP); Hideki Taniguchi, Yokohama (JP)

(73) Assignees: Corning Incorporated, Corning, NY (US); Public University Corporation Yokohama City University, Kanagawa (JP)

( * ) Notice: Subject to any disclaimer, the term of this patent is extended or adjusted under 35 U.S.C. 154(b) by 0 days.

(21) Appl. No.: 15/010,468

(22) Filed: Jan. 29, 2016

(65) Prior Publication Data
US 2016/0160175 A1 Jun. 9, 2016

Related U.S. Application Data

(62) Division of application No. 13/125,896, filed as application No. PCT/JP2009/005617 on Oct. 23, 2009, now abandoned.

(30) Foreign Application Priority Data

Oct. 24, 2008 (JP) .................................. 2008-273845

(51) Int. Cl.
*C12N 5/00* (2006.01)
*C12M 1/32* (2006.01)

(52) U.S. Cl.
CPC ........... *C12N 5/0062* (2013.01); *C12M 23/12* (2013.01); *C12N 2502/00* (2013.01); *C12N 2503/02* (2013.01); *C12N 2513/00* (2013.01)

(58) Field of Classification Search
None
See application file for complete search history.

(56) References Cited

U.S. PATENT DOCUMENTS

| | | | |
|---|---|---|---|
| 5,521,076 A | 5/1996 | Mulligan et al. | |
| 6,197,575 B1 | 3/2001 | Griffith et al. | |
| 6,458,589 B1 | 10/2002 | Rambhatla et al. | |
| 7,186,548 B2 | 3/2007 | Li | |
| 2002/0094543 A1* | 7/2002 | O'Beirne ........... G01N 33/5008 | 435/7.2 |
| 2003/0148512 A1 | 8/2003 | Fanslow, III et al. | |
| 2004/0063612 A1 | 4/2004 | Yalpani | |
| 2005/0101010 A1 | 5/2005 | Li | |
| 2006/0110826 A1 | 5/2006 | Leach et al. | |
| 2006/0252150 A1* | 11/2006 | Cheng ................. C12N 5/0606 | 435/372 |
| 2007/0258948 A1 | 11/2007 | Kolossov et al. | |
| 2008/0019949 A1 | 1/2008 | Mitchell et al. | |
| 2008/0220516 A1 | 9/2008 | Eddington et al. | |
| 2009/0042288 A1 | 2/2009 | Stoppini | |
| 2009/0075363 A1 | 3/2009 | Morimoto et al. | |
| 2009/0075366 A1* | 3/2009 | Tazaki .................. C12M 23/10 | 435/305.2 |
| 2009/0170190 A1 | 7/2009 | Nishi et al. | |
| 2011/0003389 A1* | 1/2011 | Nakazawa ............ B01L 3/5085 | 435/383 |

FOREIGN PATENT DOCUMENTS

| | | | | |
|---|---|---|---|---|
| CN | 2185755 Y | | 12/1994 | |
| JP | 8 308562 | | 11/1996 | |
| JP | 8 319317 | | 12/1996 | |
| JP | 2005027598 A | * | 2/2005 | ............ C12M 23/10 |
| JP | 2005 80607 | | 3/2005 | |
| JP | 2007-510429 | | 4/2007 | |
| JP | 2007 228818 | | 9/2007 | |

(Continued)

OTHER PUBLICATIONS

Li et al. "A novel in vitro system, the integrated discrete multiple organ cell culture (IdMOC) system, for the evaluation of human drug toxicity: comparative cytotoxicity of tamoxifen towards normal human cells from five major organs and MCF-7 adenocarcinoma breast cancer cells", Chemico-Biological Interactions 150(1): 129-136, 2004.*
Nakazawa et al., JP 2005/027598 A, EPO machine translation.*
Olsaysky et al. "Gene expression profiling and differentiation assessment in primary human hepatocyte cultures, established hepatoma cell lines, and human liver tissues." Toxicology and Applied Pharmacology 222.1 (2007): 42-56. (Year: 2007).*
International Search Report dated Jan. 12, 2010 in PCT/JP09/05617 filed Oct. 23, 2009.
English Translation of Relevant Part of Combined Chinese Office Action and Search Report dated Dec. 4, 2012 in Patent Application No. 200980142149.0.
"Micro." Available online at,http://www.merriam-webster.com/dictionary/micro>. Accessed Mar. 30, 2013.

(Continued)

*Primary Examiner* — Emily A Cordas
(74) *Attorney, Agent, or Firm* — Annie J. Kock; Cynthia A. Neal

(57) ABSTRACT

To provide a cell culture kit including cultured living cells of various donors, and a manufacturing method thereof. The cell culture kit includes a culture plate and living cells cultured thereon. The culture plate includes a plurality of microchambers (33) and living cells derived from various donors are adhered to surfaces of the plurality of microchambers (33). Specifically, living cells D1, D2, and D3 derived from various donors are adhered to the plurality of microchambers (33). In each microchamber (33), living cells derived from one donor or living cells derived from various donors may be cultured. The living cells derived from various donors are adhered and cultured in the cell culture kit as a whole, which makes it possible to provide a cell culture kit to conduct a test using cells derived from various donors.

13 Claims, 11 Drawing Sheets

(56) References Cited

FOREIGN PATENT DOCUMENTS

| JP | 2008 148702 | | 7/2008 | |
|---|---|---|---|---|
| KR | 2006-0117945 | | 11/2006 | |
| TW | 200804588 | A | 1/2008 | |
| TW | 200804589 | A | 1/2008 | |
| WO | 2004 113515 | | 12/2004 | |
| WO | WO-2006123570 | A1 * | 11/2006 | ............ C12M 23/10 |
| WO | 2006 136953 | | 12/2006 | |
| WO | 2007 105418 | | 9/2007 | |
| WO | 2007 126127 | | 11/2007 | |
| WO | 2008 002662 | | 1/2008 | |
| WO | WO 2008002662 | A2 * | 1/2008 | ............ C12N 5/0605 |
| WO | WO 2009034927 | A1 * | 3/2009 | ............ B01L 3/5085 |

OTHER PUBLICATIONS

Li Ap et al. 2004. A novel in vitro system, the integrated discrete multiple organ cell culture (IdMOC) system, for the evaluation of human drug toxicity: comparative cytotoxicity of tamoxifen towards normal human cells from five major organs and MCF-7 adenocarcinoma breast cancer cells. Chemico-Biological Interactions 150: 129-136.
Office Action as received in the corresponding Korean Patent Application No. 9-5-2015-078504602 w/partial English translation.
Nahmias Y et al. 2006. Endothelium-Mediated Hepatocyte Recruitment in the Establishment of Liver-like Tissue In Vitro Tiss Eng 12: 1627-1638.
Gupta K et al. 1997. A Novel Technique for Culture of Human Dermal Microvascular Endothelial Cells under either Serum-Free or Serum-Supplemented Conditions: Isolation by Panning and Stimulation with Vascular Endothelial Growth Factor. Exp Cell Res 230:244-251.
Salman R Khetani et al., "Microscale Culture of Human Liver Cells for Drug Development", Nature Biotechnology, vol. 26, No. 1, Jan. 1, 2008, pp. 120-126.
Sangeeta N. Bhatia et al., "Controlling Cell Interactions by Micropatterning in Co-cultures: Hepatocytes and 3T3 Fibroblasts", Journal of Biomedical Materials Research, vol. 34, No. 2, Jan. 1, 1997, pp. 189-199.
Junji Fukuda et al., "Micropatterned Cell Co-cultures using Layer-by-layer Deposition of Extracellular Matrix Components", Biomaterials, vol. 27, No. 8, Mar. 1, 2006, pp. 1479-1486.
Office Action dated Sep. 30, 2016, in Canadian Patent Application No. 2,741,493.
Summons to attend oral proceeding pursuant to Rule 115(1) EPC dated Sep. 13, 2016 in European Patent Application No. 09821832.4.
Chen-Ta Ho, et al., "Rapid heterogeneous liver-cell on-chip patterning via the enhanced field-induced dielectrophoresis trap", Lab on a chip, vol. 6, Jan. 1, 2006, XP-002591870, pp. 724-734.
European Office Action dated Jan. 20, 2016 in Patent Application No. 09 821 832.4.
Eric Leclerc et al., "Effect on Liver Cells Stepwise Microstructures Fabricated in a Photosensitive Biodegradable Polymer by Softlithography", Materials Science and Engineering C., vol. 24, No. 3, XP55241964, Apr. 1, 2004, pp. 349-354.
Wei Tan et al., "Layer-by-layer Microfluidics for Biomimetic Three-dimensional Structures", Biomaterials, Elsevier Publishers BV., vol. 25, No. 7-8, XP004475080, Mar. 1, 2004, pp. 1355-1364.
Office Action dated Jul. 26, 2016 in Korean Patent Application No. 10-2011-7011300 (with partial English translation).
Indian Office Action dated Jul. 18, 2017 in Patent Application No. 3414/CHENP/2011.
Office Action dated Sep. 26, 2017 in Canadian Patent Application No. 2,741,493.
Fukuda; "Nanotechnology MEMS De Shinka Suru Saibo Baiyo Manipulation Micro Kukan Saibo Baiyo Dish" ; Bio Industry, vol. 23, No. 2 p. 9-13 (2006)—Translation Is Attached to the Back of the Document.

* cited by examiner

1st DAY OF CULTURE

4th DAY OF CULTURE

7th DAY OF CULTURE

14th DAY OF CULTURE

21th DAY OF CULTURE

35th DAY OF CULTURE

COMPARATIVE EXAMPLE 14th DAY OF CULTURE

ALB

CYP3A4

CYP2C19

CYP2C9

CYP1A2

CYP2D6

GAPDH

IMMUNOSTAINING EXAMPLE (28th DAY OF CULTURE)

IMMUNOSTAINING COMPARATIVE EXAMPLE (30th DAY OF CULTURE)

CELL CULTURE KIT, SCREENING METHOD, AND METHOD OF MANUFACTURING CELL CULTURE KIT

CROSS-REFERENCE TO RELATED APPLICATIONS

This application is a divisional of U.S. application Ser. No. 13/125,896 filed Apr. 25, 2011, pending, which is a National Stage of PCT/JP2009/005617 filed Oct. 23, 2009 and claims the benefit of JP 2008-273845 filed Oct. 24, 2008.

TECHNICAL FIELD

The present invention relates to a cell culture kit in which living cells are cultured, a screening method, and a manufacturing method thereof.

BACKGROUND ART

A technique of using cells isolated from a tissue in testing or examination is an essential method in the biotechnology-related fields. It is widely used in diagnosing a disease or pathological condition, searching for a new drug and evaluating the efficacy of a drug, or in animal inspection, plant inspection, testing for environmental pollutants, and so on. Thus, cells and the like used in the biotechnology field have been greatly diversified.

The isolated cells are sometimes used immediately for testing, but in many cases, the cells are cultured in a culture dish or a test tube. Various examinations are carried out using the cultured cells. Cell lines in culture for use in cell culture tests are required to show drug susceptibility and toxic reaction that are similar to those obtained in a test performed in a living body, that is, a so-called in vivo test. In short, it is necessary to be able to construct an intercellular network regularly arranged on the surface of a cell culture chamber. Further, the cell lines in culture for use in cell culture tests are extremely expensive, so an improvement in survival rate and proliferation rate of cells is desired. In other words, an in vivo-like cell function is required in a cell culture chamber. Furthermore, an isolation operation to obtain primary cells is complicated, and the cell lines in culture for use in cell culture tests are expensive, so a test method using a small number of cells is desired.

Recently, discontinuation of development in the clinical testing phase has been an issue. This is due to an animal species difference in the pharmacokinetics study phase. Heretofore, in pharmacokinetics studies in the preclinical phase, drug disposition has been predicted by using an animal such as a rat, a dog or a monkey. However, it has become evident that the prediction is virtually invalid in a clinical testing using a human. Therefore, in the prediction of pharmacokinetics or the like for humans, using a human sample is the most effective and convenient way, and it is important for conducting efficient drug development and safe clinical testing.

In the pharmacokinetics study that examines drug disposition, absorption, metabolism and excretion in the liver are mainly examined, and a human sample to be used is liver slices, liver cells, liver microsomes or the like. Among those, the liver slices are not easily obtainable, and the liver microsomes can be used only for a metabolism test with limited metabolic enzymes. Thus, use of the liver cells is considered to be the most effective.

In screening, a culture dish to be used is a petri dish made of resin or a 6-well, 12-well, 48-well or 96-well plate. In general, the size of the entire plate is substantially the same, and as the number of wells increases, the size of one well decreases. A single well corresponds to a single culture dish. With the recent trend toward miniaturization, a 384-well plate having a number of culture dishes with a small diameter has also come to be used. Therefore, culture dishes which are suitable for an intended screening method come to be used. Bottoms of these culture dishes have a flat plate shape, and each of the bottom surfaces is used as a culture surface.

However, if a hitherto-used culture dish is used for culture of tissue cells, there are cases where the original function disappears and dedifferentiation occurs and where undifferentiated cells do not differentiate, which raises an issue that a target cell function is not expressed. For example, if fresh human liver cells are cultured on a normal flat plate, the function of metabolic enzymes when isolated is significantly lowered in one day or so, and therefore a drug metabolism test is conducted in four hours from seeding the cells onto the plate in some cases. There is thus a problem that it is impossible to make use for a test with long-hours culture and a problem that it is impossible to investigate long-hours metabolic stability.

To overcome the above problems, an attempt to coat a surface of a culture chamber with a biological material (glycoprotein, protein etc.) of human or animal origin (see Patent Literature 1), and an attempt to culture in polymer gel (see Patent Literature 2) have been made.

However, in the method disclosed in Patent Literature 1, there are problems such that the biological material as coating is special and high cost, it is difficult to form a uniform cell aggregate in a culture chamber, and the in vivo function cannot be maintained over a long period of time. In the method disclosed in Patent Literature 2 also, there are problems such that the size of a cell aggregate cannot be controlled, microscopic observation is not easy, and operability is complicated as a screening substrate. Further, because a commercially available dish or plate is used as a supporting chamber in both of the above methods, efficient screening with the minimum number of cells required is difficult.

CITATION LIST

Patent Literature

Patent Literature 1: Japanese Unexamined Patent Application Publication No. 8-319317
Patent Literature 2: Japanese Unexamined Patent Application Publication No. 8-308562

SUMMARY OF INVENTION

Technical Problem

As described above, for efficient drug development and safe clinical testing, many tests using human liver cells, nervous system, an intestinal epithelial system, and the like have been conducted in terms of drug toxicity, metabolism, and drug efficacy. In many cases, cell lines and primary cultured cells are used in these tests. In the case of cell lines, there is a problem that in vivo functions are not reflected. On the other hand, primary cultured cells can reflect in vivo functions, but the individual difference becomes a problem. To overcome the problem of individual difference, it has been studied to use living cells including floating cells which include liver cells from various donors, and to obtain averaged data. However, there is a problem that the life-span of floating cells is short, which makes it impossible to use the floating cells for a test over a long period of time.

The present invention has been made to solve the above-mentioned problems, and therefore has an object to provide a cell culture kit in which living cells from various donors are cultured, a screening method, and a manufacturing method thereof.

Solution to Problem

An aspect of a cell culture kit according to the present invention is a cell culture kit including a cell culture plate and living cells cultured thereon. The cell culture plate includes a plurality of micro spaces, and living cells derived from various donors are adhered to surfaces of the plurality of micro spaces. This makes it possible to provide a kit for screening in which living cells derived from various donors are adhered to a single cell culture plate.

The living cells derived from various donors may include two or more types of cells. This makes it possible to reproduce a tissue-like structure formed by various types of living cells.

Specifically, the living cells derived from various donors or living cells derived from a single donor are adhered to each of the plurality of micro spaces.

For example, living cells derived from various donors are adhered to at least two adjacent micro spaces. Alternatively, living cells derived from a single donor are adhered to at least two adjacent micro spaces.

Further, it is preferred that the plurality of micro spaces have dimensions to allow a cell population of a three-dimensional structure to be isolated, the cell population being obtained by culture of a desired number of cells.

It is preferred that the living cells be seeded in the plurality of micro spaces at a cell seeding density of $1 \times 10^2$ to $1 \times 10^6$ cells/cm$^2$, more preferably at a cell seeding density of $1 \times 10^4$ to $1 \times 10^6$ cells/cm$^2$. It is preferred that a cell mass having the living cells accumulated therein be formed in each of the plurality of micro spaces, more specifically, it is preferred that the cell mass have a diameter of 30 to 200 μm.

It is preferred that the living cells be one of tissue precursor cells, tissue stem cells, cells differentiated from ES cells, and cells differentiated from iPS cells.

Alternatively, it is preferred that the living cells include liver cells. It is more preferred that the liver cells be one of tissue precursor cells, tissue stem cells, cells differentiated from ES cells, and cells differentiated from iPS cells, and that the living cell including the liver cells be isolated from hepatic tissues of various donors.

Further, an aspect of a screening method according to the present invention is a screening method for evaluating drugs by using above-described cell culture kit.

Furthermore, an aspect of a method of manufacturing a cell culture kit according to the present invention is a method of manufacturing a cell culture kit which includes a culture plate including a plurality of micro spaces and living cells cultured thereon. The method of manufacturing a cell culture kit includes: seeding living cells derived from various donors in the plurality of micro spaces; and culturing the seeded living cells.

Advantageous Effects of Invention

According to the present invention, it is possible to provide a cell culture kit in which living cells of various donors are cultured, a screening method, and a method of manufacturing a cell culture kit.

DESCRIPTION OF EMBODIMENTS

Figure 1:
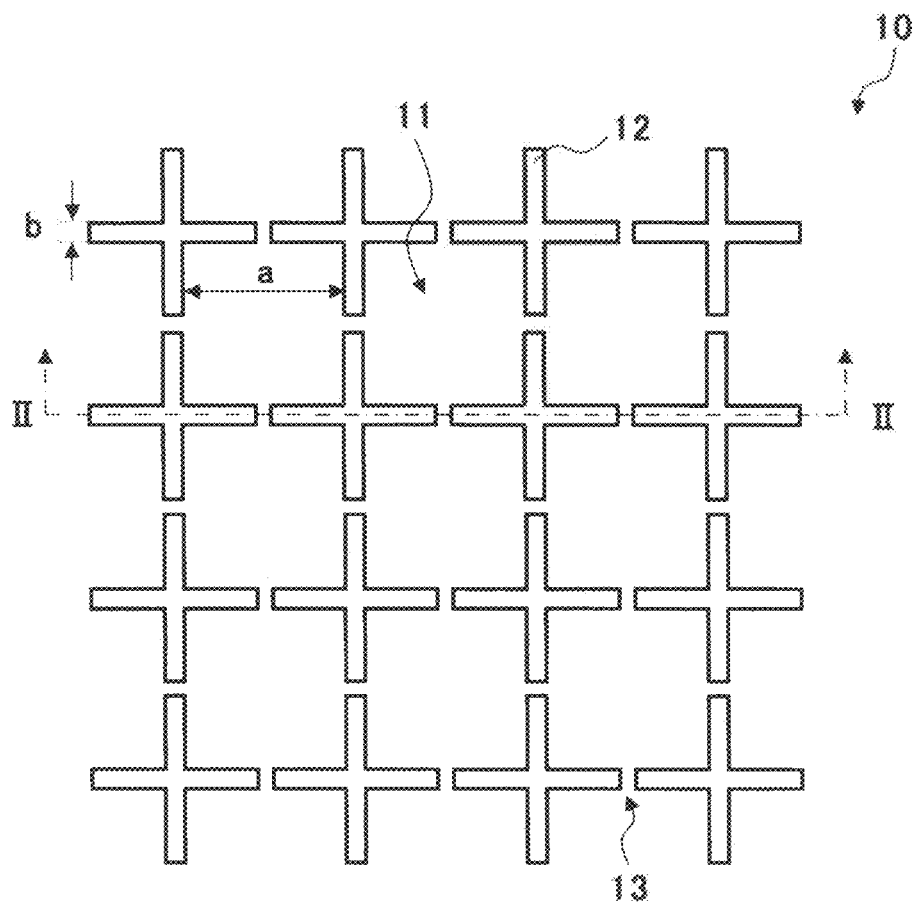
FIG. 1 is a plane view showing a structure of a cell culture chamber according to an embodiment.

A cell culture kit according to the present invention includes a cell culture plate and living cells cultured thereon, and uses a plurality of microchambers which are included in the culture plate. Living cells derived from various donors are adhered to surfaces of the plurality of microchambers. Since the living cells are cultured so as to maintain cell functions, it is necessary to use suitable microchambers, which are units for culturing the living cells. Examples of the cell culture chamber to be used for the cell culture kit according to the present invention are given below.

A cell culture chamber has a concave-convex pattern, i.e., a plurality of microchambers formed therein. This permits cells to grow in three dimensions, like in a living body, and also permits cells to be cultured in aggregated form with no variation in each microchamber. The height of side walls (convex portions) for partitioning the microchambers is optimized, thereby making it possible to culture aggregated living cells (for example, a mass of liver cells) exclusively within the microchambers. Note that the term "micro space" refers to a space formed by a microchamber, more specifically to a space formed by a concave-convex pattern formed on a plane surface. Hereinafter, the microchamber and the micro space are not particularly distinguished from each other.

The dimensions of the microchambers each surrounded by the side walls have to be set within the optimum range for culturing cells. If the bottom area of each microchamber is too large, cells are thinly elongated and fail to show a three-dimensional structure, as in the culture on a flat plate. If, on the other hand, the bottom area of each microchamber is too small, it cannot accommodate cells. Accordingly, the dimensions of the space structure are preferably in a range capable of containing one or a plurality of cells according to cell species to be cultured. In the case of forming the mass of liver cells in which a plurality of cells is accumulated, the dimensions are preferably in a range capable of containing the mass of liver cells.

The height of each side wall has to be set within the optimum range for preventing the cells cultured in the microchambers from moving to the adjacent microchambers. If the height of each side wall is too low, the cells run on the side wall, and thus such side wall is unsuitable for culture. If the height of each side wall is too high, the production thereof is difficult and material diffusion becomes difficult, leading to a deterioration of the culture environment. Therefore, the height of each side wall is preferably in the range capable of continuously and stably culturing cells, which are arranged in the microchambers according to cell species, within the microchambers.

In addition, openings are formed in the side walls to obtain a structure in which the plurality of microchambers communicates with each other, thereby making it possible to supply oxygen and nutrients to cells and remove waste products from the cells effectively. Note that the height of the side walls, the dimensions of the microchambers, and the width of the openings are appropriately set according to cell species to be cultured, thereby enabling application to various culture systems.

In this specification, the term "living cells" refers to cells (primary cultured cells) which are isolated from a living body tissue and which are not passaged. The living cells include fresh cells and frozen cells. The living cells also include cell lines, other ES cells (Embryonic Stem cells), and so on.

As the living cells, one or more types of cells are preferably selected from among liver cells (parenchymal liver cells), hepatic stellate cells, fat cells, skeletal muscle cells, cardiac muscle cells, smooth muscle cells, cartilage cells, bone cells, nerve cells, glia cells, Schwann cells, beta cells of pancreas, epidermal cells, vascular endothelial cells, fibroblast, and mesenchymal cells. These cell species may be primary cultured cells, tissue precursor cells, tissue stem cells, cells differentiated from ES cells, or cells differentiated from iPS cells.

Embodiment

Hereinafter, an embodiment of the present invention is described. However, the present invention is not limited to the following embodiment. Further, to clarify the explanation, the following description and the drawings are appropriately simplified.

Figure 2:
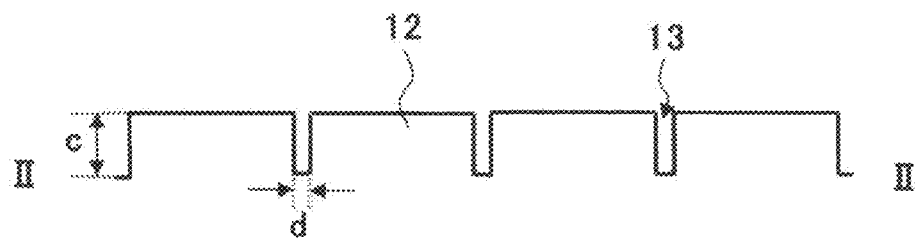
FIG. 2 is a cross-sectional view along the line II-II showing the structure of the cell culture chamber according to an embodiment.

First, a cell culture chamber for use in a cell culture kit according to an embodiment will be described, and subsequently, an exemplary structure of the cell culture kit will be described. To begin with, an exemplary structure of the cell culture chamber will be described with reference to FIGS. 1 and 2. FIG. 1 is a plane view showing the structure of the cell culture chamber according to this embodiment, and FIG. 2 is a cross-sectional view along the line II-II in FIG. 1. As shown in FIG. 1, a cell culture chamber 10 includes microchambers 11, side walls 12, and openings 13. The plurality of side walls 12 is formed in a net shape on the culture surface of the cell culture chamber 10, and spaces surrounded by the side walls 12 serve as the microchambers 11. Additionally, each of the openings 13 is formed at a central portion of each side of the side walls 12 which are formed on four sides of each of the microchambers 11.

FIG. 1 shows a width "a" of the bottom of each of the microchambers 11, a width "b" and a height "c" of each of the side walls 12 for partitioning the microchambers 11, and a width "d" of each of the openings 13 for allowing communication between the microchambers 11 adjacent to each other. The term "bottom area" of the present invention refers to a projected area which is formed when parallel light is irradiated to the bottom of the chamber from above in the direction perpendicular to the horizontal plane of the microchmaber opening (the same plane as the top surfaces of the side walls 12). For example, if the bottom of the microchamber is U-shaped, the bottom area has a shape formed by projecting parallel light incident on the bottom from above in the direction perpendicular to the opening plane. In the case of a circle or an ellipse, a major axis of a projected bottom is a distance between intersections of a long axis which runs through the center of gravity thereof and the circumference, and a minor axis of the projected bottom is a distance between intersections of a short axis which runs through the center of gravity thereof and the circumference. In the case of a polygon, the major axis and the minor axis of the projected bottom respectively correspond to a long axis and a short axis of an extrapolated circle or an extrapolated ellipse which is set so as to minimize the difference between areas of the polygon and the extrapolated circle or the extrapolated ellipse and which runs through all vertexes of the polygon. If an extrapolated circle or an extrapolated ellipse which runs through all vertexes of the polygon cannot be traced, the major axis and the minor axis respectively correspond to a long axis and a short axis of an approximate circle or an approximate ellipse which runs through the largest number of vertexes.

The bottom shape of each of the microchambers 11 is not particularly limited, and various shapes other than a square, a circle, and a polygon can be employed. In cell culture for reproducing a liver function in vivo, the bottom area is preferably 0.01 mm$^2$ to 0.1 mm$^2$. In this case, the major axis of the bottom is preferably 1 to 1.5 times the minor axis thereof. An isotropic shape is more preferably used. If a square is employed, for example, in the case of forming a mass of liver cells having an equivalent diameter of 100 μm, the length of one side thereof is preferably 100 μm to 300 μm.

An angle formed between the horizontal plane and the side walls 12 of each of the microchambers 11 should be set to an angle at which cells are prevented from running on the microchambers. Accordingly, 50% or more of an upper portion of a side surface preferably has an angle of 80° to 90°, and more preferably, 85° to 90°.

The height "c" of each of the side walls 12 may be arbitrarily set as log as the cells cultured in the microchambers 11 are prevented from running on and moving to the adjacent microchamber 11. In the case of forming a mass of liver cells having an equivalent diameter of 100 μm, the height "c" is preferably 50 μm to 150 μm, for example.

Figure 3:
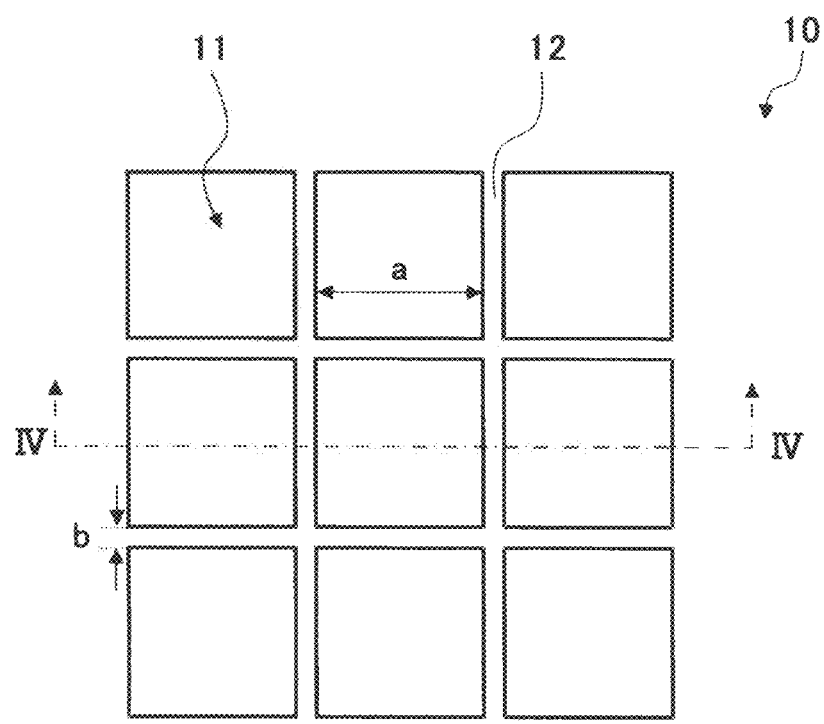
FIG. 3 is a plane view showing another structure of a cell culture chamber according to an embodiment.
Figure 4:
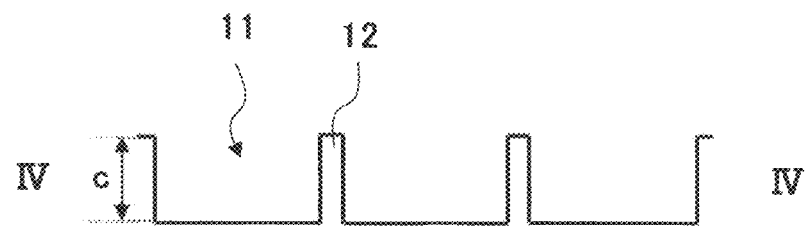
FIG. 4 is a cross-sectional view along the line IV-IV showing another structure of the cell culture chamber according to an embodiment.

The width "d" of each of the openings 13 for allowing communication between the microchambers 11 adjacent to each other is preferably set to a width in which cells are prevented from moving from the microchamber 11, in which the cultured cell is first seeded, to the adjacent microchamber 11. When the equivalent diameter of the cultured cell is 20 μm, for example, the width is preferably 5 to 15 μm. Note that the openings 13 are not necessarily formed. As shown in FIGS. 3 and 4, the four sides of each of the microchambers 11 may be entirely surrounded by the side walls 12. Here, FIG. 3 is a plane view showing another structure of the cell culture chamber according to this embodiment, and FIG. 4 is a cross-sectional view along the line IV-IV in FIG. 3.

In FIG. 3, the width "a" of the bottom surface of the microchamber 11, and the width "b" and the height "c" of the side wall 12 for partitioning the microchambers 11 are shown. It is necessary to satisfy 3 μm≤b≤15 μm and c/b≥2. If the width "b" of the side wall 12 is more than 15 μm, a cell adheres to the top surface of the side wall, which is unsuited to culture. On the other hand, if the width "b" of the side wall 12 is less than 3 μm, preparation is difficult. If the height of the side wall is too low, a cell goes over the side wall, which is unsuited to culture. If the height "c" of the side wall 12 is less than two times the width "b" of the side wall 12, a cell cultured in the microchamber 11 goes over it and moves to the adjacent microchamber 11. Further, specifically, when human fetal liver cells are layered in a square microchamber with one side of 100 μm, the height "c" of the side wall 12 is preferably 15 μm to 300 μm, and more preferably 50 μm to 150 μm. If the height "c" of the side wall is too high, preparation is difficult and further the material is hard to diffuse, which degrades the culture environment. The side wall 12 may have a multi-step shape.

Figure 5:
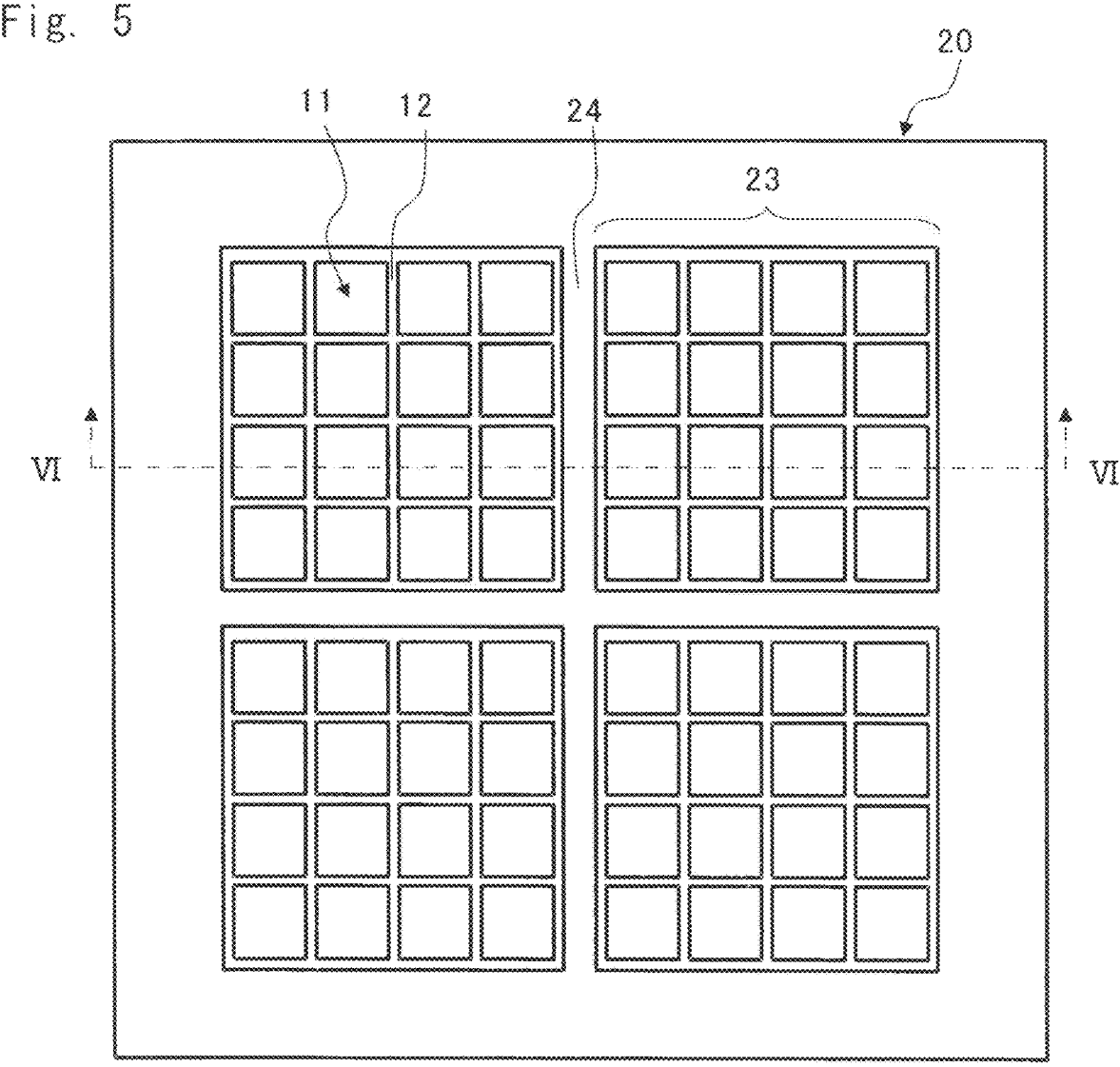
FIG. 5 is a plane view showing still another structure of a cell culture chamber according to an embodiment.
Figure 6:
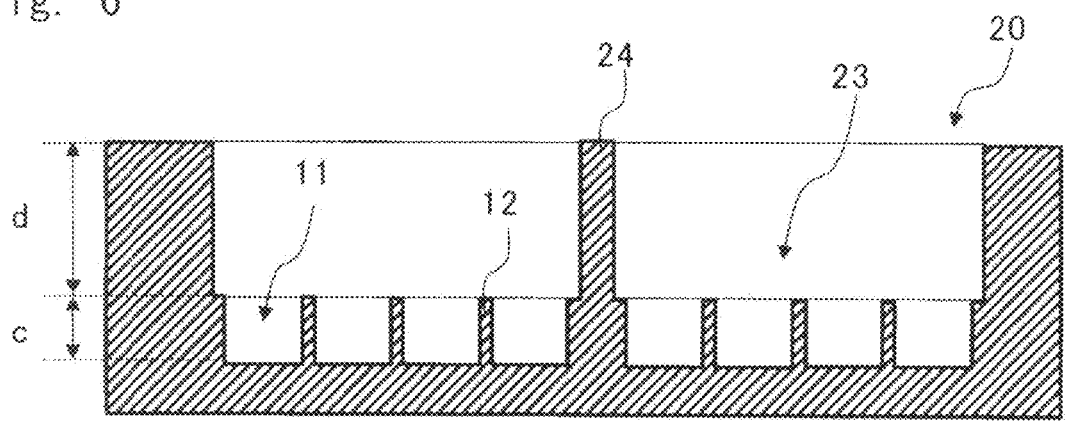
FIG. 6 is a cross-sectional view along the line VI-VI showing still another structure of the cell culture chamber according to an embodiment.

The cell culture unit may have partitioned spots each made up of a plurality of microchambers required for one screening as shown in FIGS. 5 and 6 in order to minimize the number of cells required. For example, in the case of using a microchamber in a square shape with one side of 200 μm and a height of 50 μm which provides a high differentiation efficiency when the minimum number of cells required for screening is about 1000, nine microchambers are required; therefore, by preparing a spot in which the space is partitioned into nine microchambers and providing a plurality of spots, it is possible to perform high-throughput screening that allows simultaneous examination of a plurality of reagents or pharmaceutical agents.

FIG. 5 is a plane view showing another structure of a cell culture unit according to the embodiment, and FIG. 6 is a cross-sectional view along line IV-IV in FIG. 5. FIG. 5 shows the side wall 24 that partitions a plurality of microchambers and a partitioned spot 23. The height "d" of the side wall 24 may be set so that the capacity can keep a supernatant fluid such as a culture solution or a reaction solution without drying, and it can be defined appropriately.

A method for forming the concave-convex pattern on the cell culture chamber is not particularly limited, but methods such as transfer molding using a mold, three-dimensional stereolithography, precision machining, wet etching, dry etching, laser processing, and electrical discharge machining may be employed. It is preferable to appropriately select these production methods in view of the intended use, required processing accuracy, costs, and the like of the cell culture chamber.

As a specific example of the transfer molding method using a mold, a method for forming the concave-convex pattern by resin molding using a metal structure as a mold may be employed. This method is preferred because it is capable of reproducing the shape of the metal structure on a resin as the concave-convex pattern with a high transcription rate, and because the raw material cost can be reduced by using a general-purpose resin material. Such a method using a mold of a metal structure is superior in terms of low cost and achieving satisfactorily high dimensional accuracy.

As methods of producing the metal structure, for example, plating treatment, precision machining, wet etching, dry etching, laser processing, and electrical discharge machining on a resist pattern produced by photolithography or a resin pattern produced by three-dimensional stereolithography may be employed. The methods may be appropriately selected in view of the intended use, required processing accuracy, costs, and the like.

As methods of forming the concave-convex pattern on a resin using the metal structure, which is obtained as described above, as a mold, injection molding, press molding, monomer casting, solvent casting, hot embossing, or roll transfer by extrusion molding may be employed, for example. It is preferable to employ injection molding in view of its productivity and transcription property.

Materials for forming a cell culture chamber are not particularly limited as long as the materials have self-supporting properties. For example, synthetic resin, silicon, or glass may be employed. A transparent synthetic resin is preferably used as a material in view of costs and cell visibility under microscopical observation. Examples of the transparent synthetic resin include acrylic resins such as polymethylmethacrylate or methyl methacrylate-styrene copolymer, styrene resin such as polystyrene, olefin resin such as cycloolefin, ester resins such as polyethylene terephthalate and polylactic acid, silicone resin such as polydimethylsiloxane, and polycarbonate resin. These resins may contain various additives such as colorant, dispersing agent, and thickening agent, unless the transparency is impaired.

In the cell culture chamber, surface treatment may be performed on the surface side of the concave-convex pattern and a modified layer and/or a coating layer may be formed for the purpose of improving the hydrophilic properties, biocompatibility, cellular affinity, and the like of the chamber surface. A method for forming the modified layer is not particularly limited unless a method with which the self-supporting properties are impaired and a method causing extreme surface roughness of 100 μm or more are employed. Methods, for example, chemical treatment, solvent treatment, chemical treatment such as introduction of a graft polymer by surface graft polymerization, physical treatment such as corona discharge, ozone treatment, or plasma treatment may be employed. In addition, though a method for forming the coating layer is not particularly limited, methods, for example, dry coating such as sputtering or vapor deposition and wet coating such as inorganic material coating or polymer coating may be employed. In order to pour a culture solution without mixing air bubbles therein, it is desirable to impart the hydrophilic properties to the surface of the concave-convex pattern. As a method for forming a uniform hydrophilic membrane, inorganic vapor deposition is preferably employed.

When the cellular affinity is taken into consideration, it is more preferable to coat cytophilic proteins such as collagen and fibronectin. In order to uniformly coat a collagen aqueous solution or the like, it is preferable to perform the coating after the above-mentioned hydrophilic membrane is formed. In hepatocyte cultures, in general, it is desirable to culture cells on an extracellular matrix surface by replicating the in vivo environment. Accordingly, it is particularly preferable to dispose an organic film made of extracellular matrix suitable for cultured cells after an inorganic hydrophilic membrane is uniformly formed as described above.

In a cell culture method using the cell culture chamber described above, an appropriate number of cells need to be seeded so that the cells are arranged exclusively within the microchambers for culturing cells and that morphologies and functions similar to those of the living body are developed within the space. A cell seeding density of $1.0 \times 10^2$ to $1.0 \times 10^6$ cells/cm$^2$ is preferably used and a cell seeding density of $1.0 \times 10^4$ to $1.0 \times 10^6$ cells/cm$^2$ is more preferably used. When each microchamber is a square which is 200 μm on a side, for example, a cell seeding density of $5.0 \times 10^4$ to $5.0 \times 10^5$ cells/cm$^2$ is preferably used. Under such conditions, a mass of liver cells having a diameter of 30 to 200 μm can be obtained.

Figure 7:
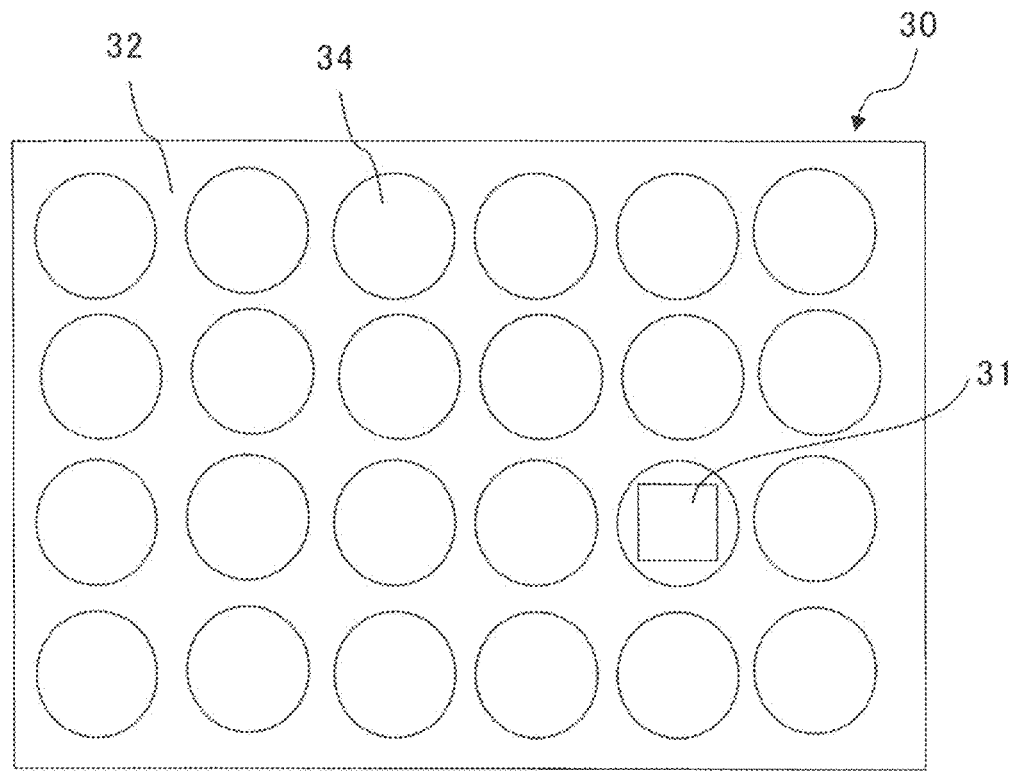
FIG. 7 is a view showing an exemplary cell culture kit in which a plurality of cell culture chambers are arranged.

Subsequently, an exemplary structure of the cell culture kit according to this embodiment will be described referring to FIGS. 7 to 10. FIG. 7 is a view showing an exemplary structure of the cell culture kit. A cell culture kit 30 includes a culture plate 32 with a flat shape. The culture plate 32 includes a plurality of culture dishes 34. A cell culture chamber 31 is arranged in each of the culture dishes 34. The number of the culture dishes 34 set in one culture plate 32 is determined depending on a method of screening, cell types to culture, or the number of cells to be used for a test. The culture plate 32 includes at least one cell culture chamber 31. The cell culture chamber 31 may have any one of three types of structures shown in FIGS. 1 to 6, for example. Other structures that satisfy the conditions of the concave-convex pattern described above may also be used. The bottom of the culture dish 34 has a flat plate shape, and the bottom surface of the cell culture chamber 31 is used as a culture surface.

Figure 8:
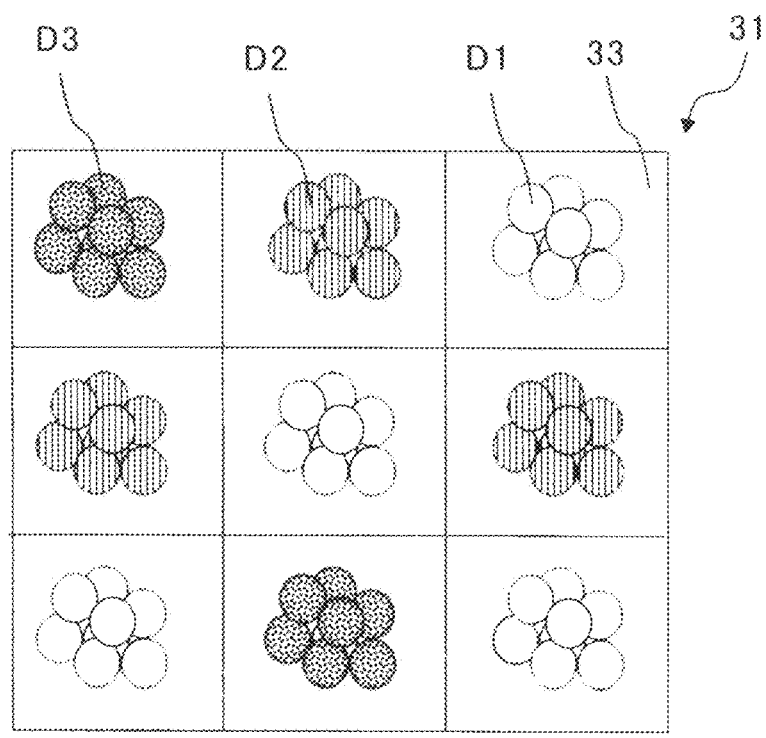
FIG. 8 is a view showing an exemplary state in which living cells are cultured in a plurality of microchambers.
Figure 9:
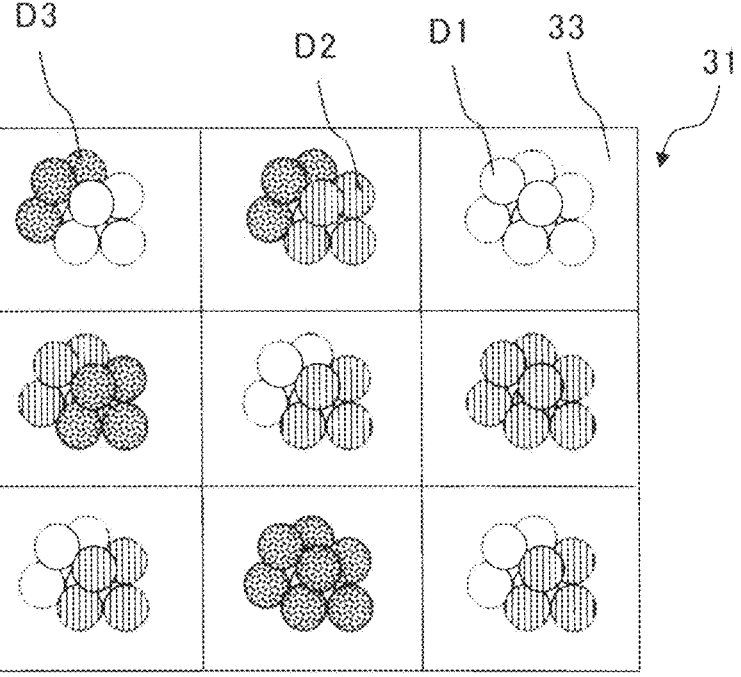
FIG. 9 is a view showing another exemplary state in which living cells are cultured in a plurality of microchambers.
Figure 10:
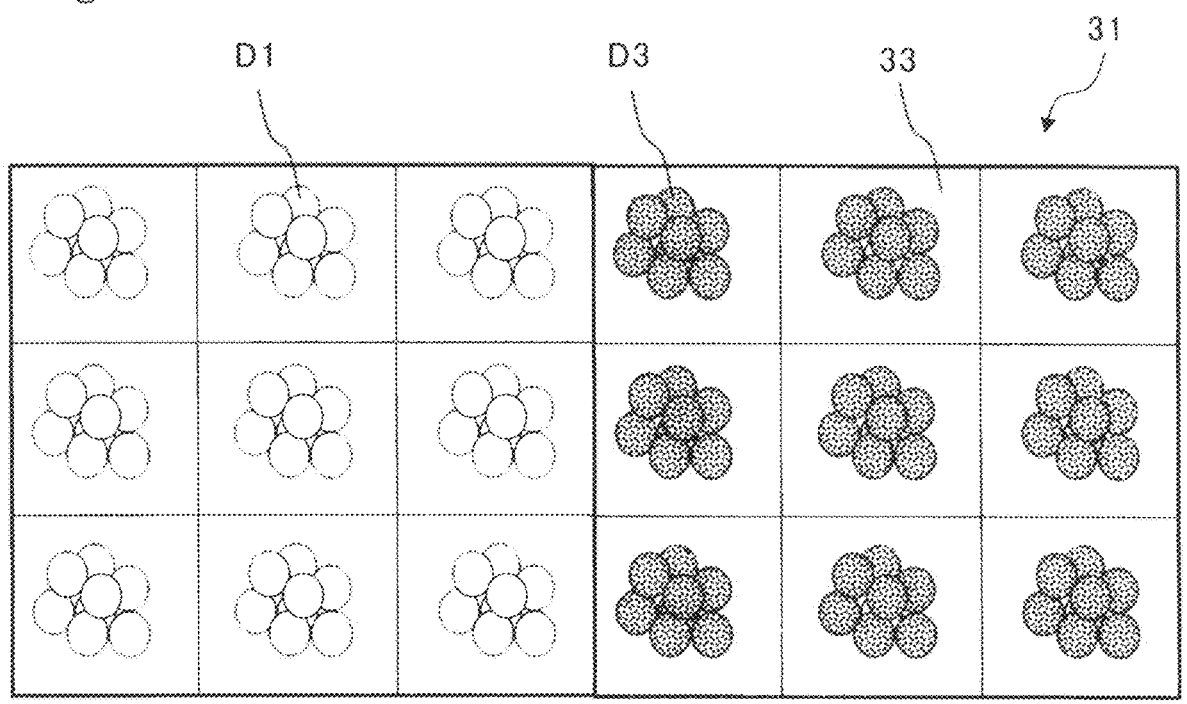
FIG. 10 is a view showing still another exemplary state in which living cells are cultured in a plurality of microchambers.
Figure 11A:
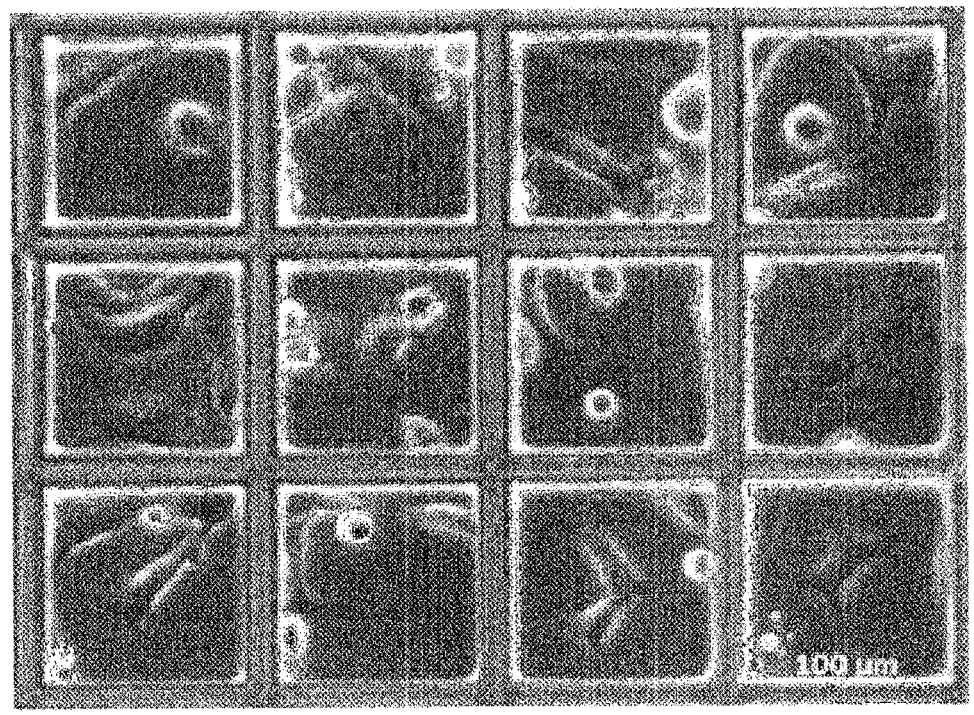
FIG. 11A is a photograph showing a result of morphology observation on the 1st day of culture of an example.
Figure 11B:
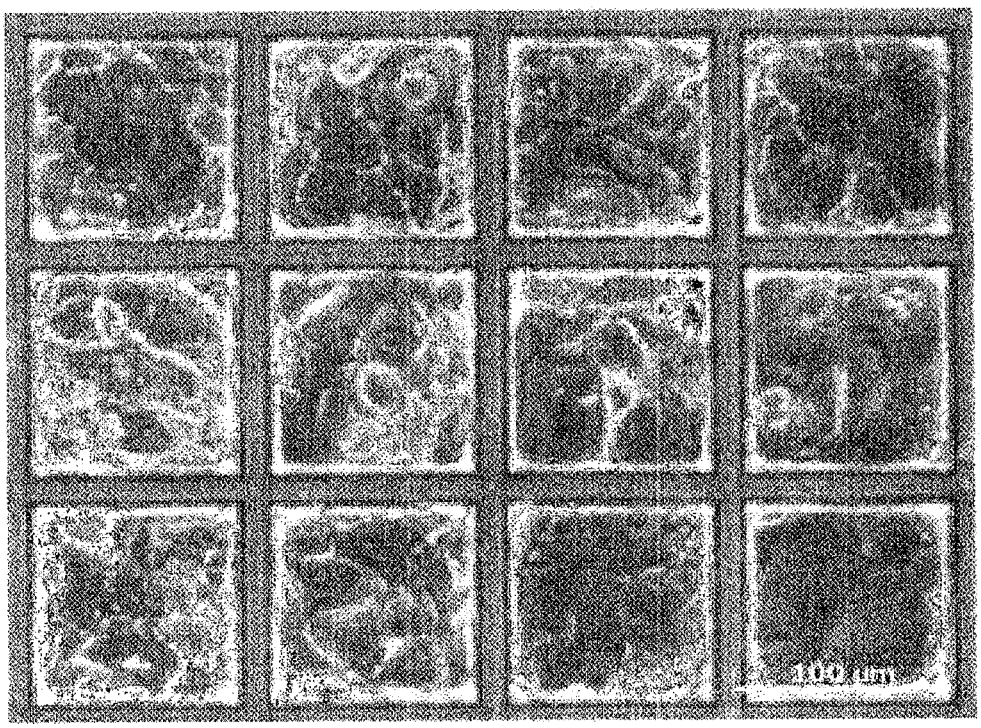
FIG. 11B is a photograph showing a result of morphology observation on the 4th day of culture of the example.
Figure 11C:
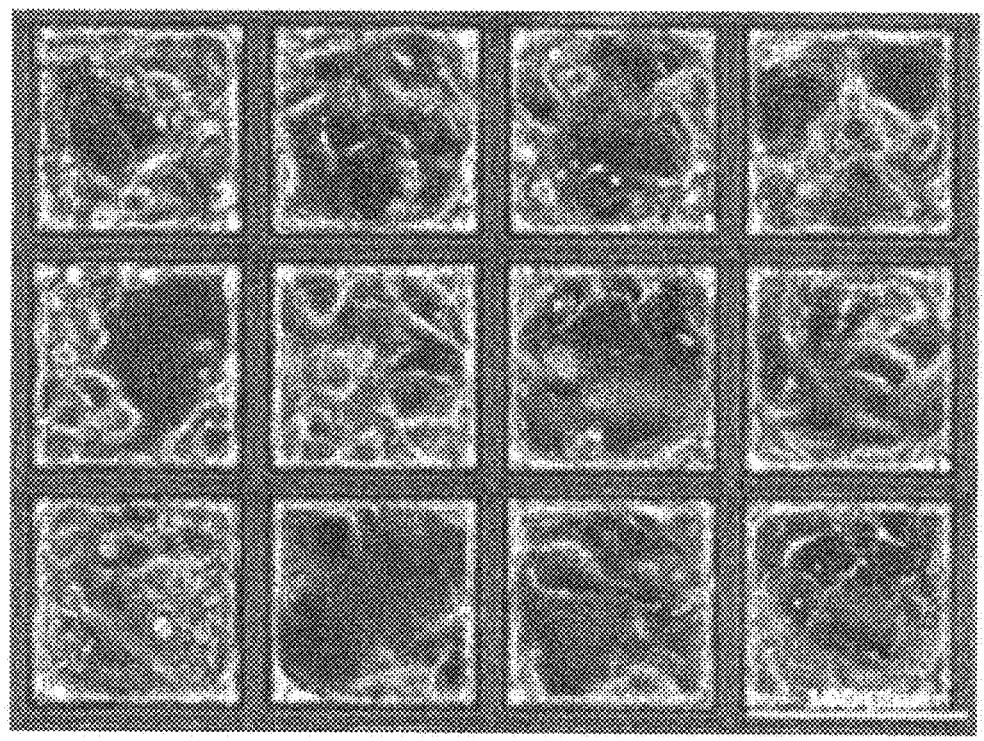
FIG. 11C is a photograph showing a result of morphology observation on the 7th day of culture of the example.
Figure 11D:
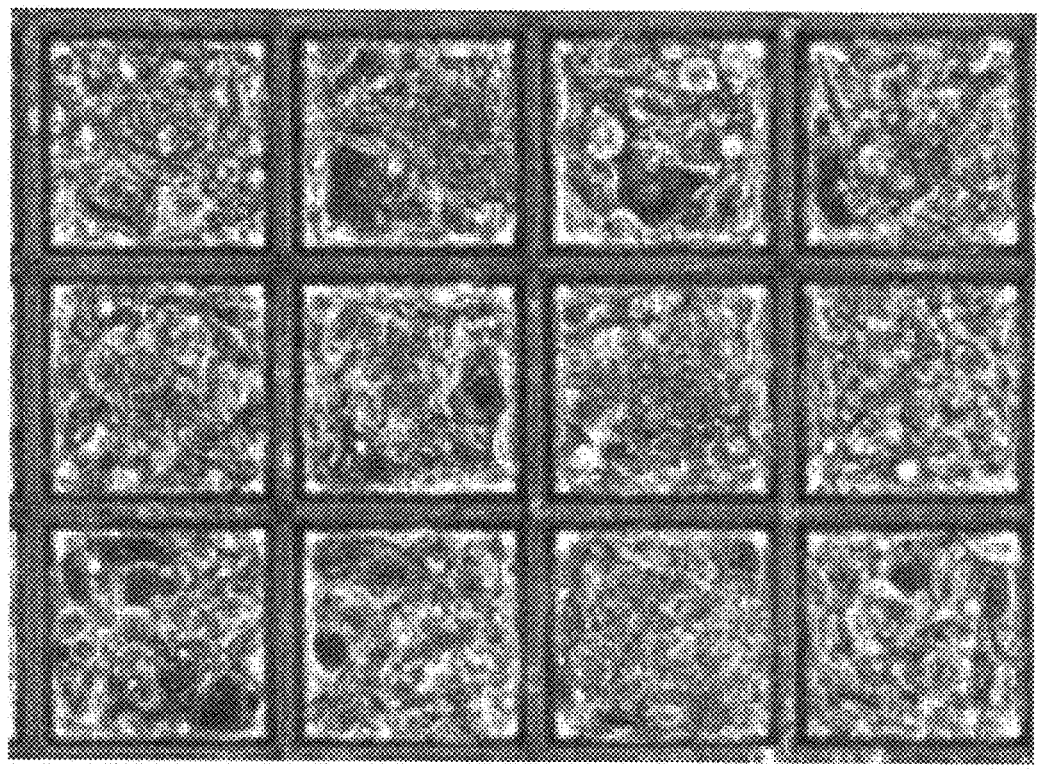
FIG. 11D is a photograph showing a result of morphology observation on the 14th day of culture of the example.
Figure 11E:
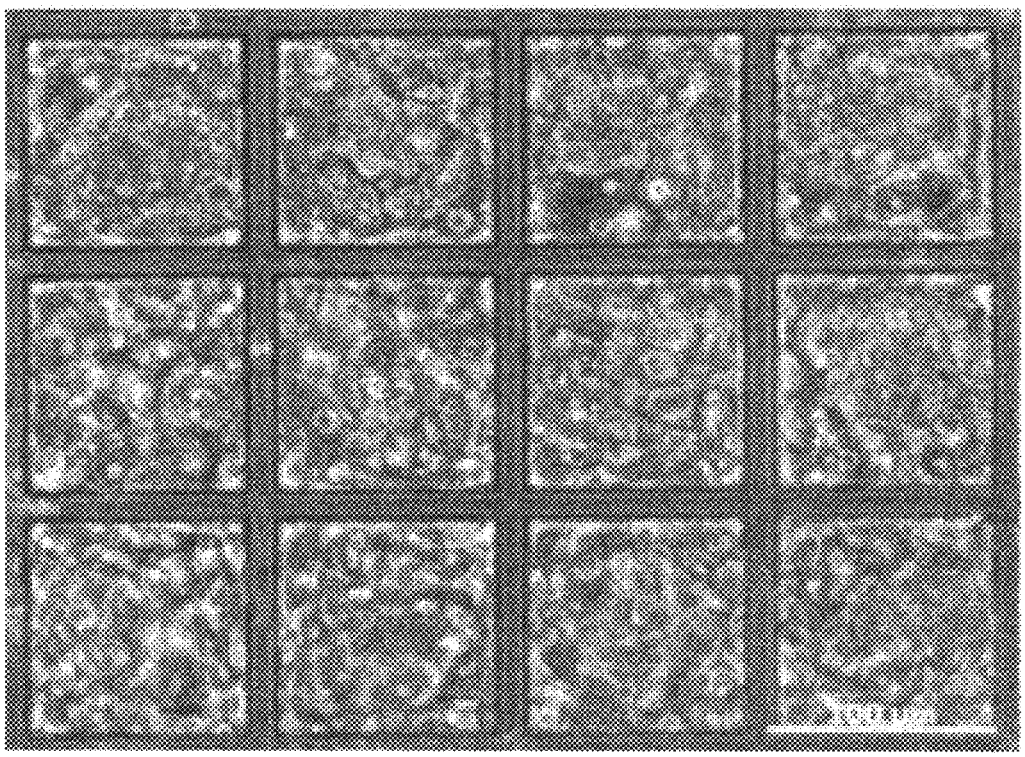
FIG. 11E is a photograph showing a result of morphology observation on the 21st day of culture of the example.
Figure 11F:
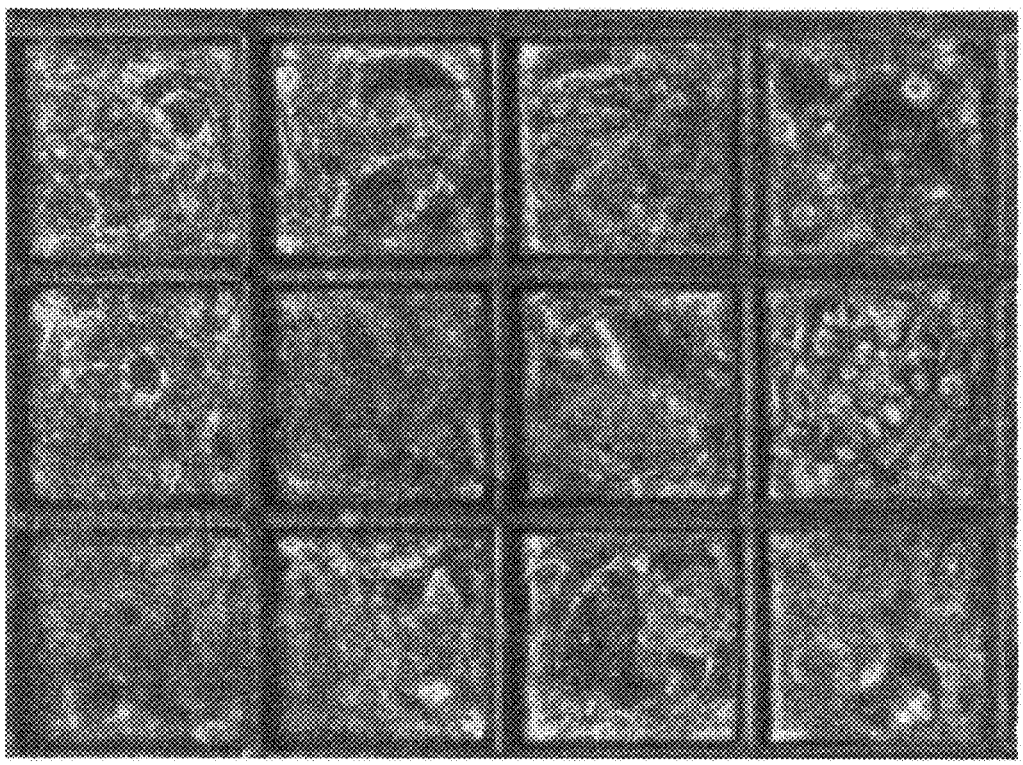
FIG. 11F is a photograph showing a result of morphology observation on the 35th day of culture of the example.

FIGS. 8 to 10 show exemplary states in which living cells are cultured in a plurality of microchambers and differences among donors of seeded cells. In FIGS. 8 to 10, each rectangle represents the microchamber 33. FIGS. 8 and 9 show a case where the cell culture chamber 31 includes nine microchambers 33. FIG. 10 shows a case where the cell culture chamber 31 includes eighteen microchambers 33. Further, references D1 to D3 represent cultured cells, and various patterns are used to show differences among donors of D1, D2, and D3.

FIG. 8 shows a case where cells derived from one donor are adhered to each of the microchambers 33, and the donor of the cells in the one microchamber 33 is different from that of cells in adjacent microchambers 33. FIG. 9 shows a case where a mixture of living cells derived from various donors is adhered in some parts, and living cells derived from a single donor are adhered in other parts. This case shows an example where living cells derived from two donors are adhered to one microchamber 33. FIG. 10 shows a case where the plurality of microchambers 33 are divided into two divisions, and living cells of a first type donor are adhered to one division and living cells of a second type donor are adhered to the other division. Note that the plurality of microchambers 33 may be divided into three or more divisions. It is possible to confirm differences in testing result between various donors by adhering cells of a desired donor to each division.

Though, FIGS. 8 to 10 show exemplary arrangements of the living cells derived from various donors, the arrangement is not limited thereto. Other arrangements may also be employed as long as the living cells derived from various donors are adhered to and cultured in the plurality of microchambers 33 included in the cell culture kit 30. In particular, a plurality of living cells derived from various donors may be adhered to each of the microchambers 33. The number of types of donors of living cells to be adhered to one microchamber 33 may be three or more. Further, living cells derived from a single donor may be adhered to each of the microchambers 33, and the entire cell culture kit (or a single cell culture chamber 31) may contain living cells of a plurality of donors. More alternatively, living cells derived from a single donor are adhered to each one of the cell culture chambers 31, and living cells derived from various donors may be adhered to the plurality of cell culture chambers 31 as a whole. In other words, it is sufficient that living cells derived from various donors are adhered to the cell culture kit 30.

The living cells derived from various donors are cultured in the state of being adhered to the surface of each of the microchambers 33 of the cell culture kit 30. In the microchambers, the living cells are accumulated to form a cell mass. The cell mass is cultured up to a desired size. For example, the diameter of a cell mass to be cultured is 30 to 200 μm. The size of the microchamber is also determined depending on the size of the cell mass.

Parenchymal cells derived from various donors are used as the living cells to be cultured in the microchambers. The parenchymal cells to be used are tissue precursor cells, tissue stem cells, cells differentiated from ES cells, parenchymal cells differentiated from iPS cells (induced pluripotent stem cells), or parenchymal cells derived from a living body.

When various types of cell species are used, one type of parenchymal cells and other cell species are mixed and cultured. In this case, as for the derivation of cell species, parenchymal cells of various donors and other cell species derived from one donor, or parenchymal cells derived from one donor and other cell species derived from a donor different from the donor of the parenchymal cells may be used. As other cell species to be used, one or more cell species are selected from hepatic stellate cells, vascular endothelial cells, fibroblasts, and mesenchymal cells. Parenchymal cells, hepatic stellate cells, vascular endothelial cells, fibroblasts, and mesenchymal cells to be used are tissue precursor cells, tissue stem cells, cells differentiated from ES cells, cells differentiated from iPS cells (induced pluripotent stem cells), or cells derived from a living body.

A culture medium to be used is a medium containing nutrient components, such as a nutrient factor, a blood serum, or a secretion solution from cells. In the case of the secretion solution from cells, it is also possible to use a method of setting a chamber where cells are cultured on a membrane such as a cell culture insert.

As described above, according to an aspect of the embodiment of the present invention, it is possible to provide a cell culture kit where living cells of various donors are adhered and cultured within a single chamber (within the cell culture kit). The cell culture kit includes a plurality of microchambers. As described above, the plurality of microchambers have a structure which allows the in vivo functions of the living cells to be maintained for a long term. Therefore, it is possible to provide living cells having in vivo-like cell functions. Additionally, it is possible to obtain testing results of various donors on a single chip. This makes it possible to efficiently carry out tests using cells derived from various donors over a long period of time.

EXAMPLES

<Results of Culturing Various Types of Cells Derived from Various Donors (Such as Parenchymal Liver Cells and Non-Parenchymal Liver Cells) in a Plate Including Micro Spaces>

1. Cell Preparation 1-1. Culture of Liver Cells (Cell Growth)

Transformed cells (hereinafter referred to as "transformed liver cells"), which were obtained by introducing a BMI1 gene into human hepatic stem cells (Accession Number FERM BP-11108, National Institute of Advanced Industrial Science and Technology, International Patent Organism Depositary), were seeded to a type-IV collagen coated dish (manufactured by Becton, Dickinson and Company) and cultured.

As a culture medium, a DMEM and nutrient mixture F-12 Ham medium (DMEM/F12 1:1 mixture) mixed with 10% fetal bovine serum (FBS), human γ-insulin (1.0 μg/ml), nicotinamide (10 mmol/l), dexamethasone ($1 \times 10^{-7}$ mol/l), and L-glutamine (2 mmol/l) was used. Culture was carried out in an incubator at 37° C. and 5% $CO_2$, and the culture medium was changed every five days.

1-2. Culture of Vascular Endothelial Cells (Cell Growth)

Human vascular endothelial cell lines derived from a donor different from the donor of the transformed liver cells were seeded a non-coated dish for cell culture (manufactured by Becton, Dickinson and Company) and cultured.

As a culture medium, a DMEM and nutrient mixture F-12 Ham medium (DMEM/F12 1:1 mixture) mixed with 10% fetal bovine serum (FBS), human γ-insulin (1.0 μg/ml), nicotinamide (10 mmol/l), dexamethasone ($1 \times 10^{-7}$ mol/l), and L-glutamine (2 mmol/l) was used. Culture was carried out in an incubator at 37° C. and 5% $CO_2$, and the culture medium was changed every five days.

1-3. Preparation of Cell Suspension

Each of the cells, which were cultured as described in the items 1-1 and 1-2, was detached using a 0.25% trypsin solution and collected, and was then dispersed into a culture medium.

As the culture medium, a DMEM and nutrient mixture F-12 Ham medium (DMEM/F12 1:1 mixture) mixed with 10% fetal bovine serum (FBS), human γ-insulin (1.0 μg/ml), nicotinamide (10 mmol/l), dexamethasone ($1 \times 10^{-7}$ mol/l), and L-glutamine (2 mmol/l) was used. Each of the cells was stained with trypan blue to count the number of living cells.

2. Culture Test (Example, Comparative Example)

2-1 <Example 01>

The transformed liver cells and vascular endothelial cells, which were obtained as described in the item 1-3, were mixed at a mixing ratio of 1:3, and were seeded in a culture chamber at a cell density of $3.75 \times 10^4$ cells/$cm^2$. A 24-well type culture chamber which has the concave-convex pattern as shown in FIGS. 3 and 4 and which includes micro spaces having dimensions of a=100 μm and c=50 μm was used as the culture chamber.

2-2 <Comparative Example 01>

The transformed liver cells, which were obtained as described in the item 1-3, were seeded in a culture chamber at a cell density of $3.75 \times 10^4$ cells/$cm^2$. A 24-well type culture chamber which has the concave-convex pattern as shown in FIGS. 3 and 4 and which includes micro spaces having dimensions of a=100 μm and c=50 μm was used as the culture chamber.

2-3 <Comparative Example 02>

The transformed liver cells, which were obtained as described in the item 1-3, were seeded in a 24-well cell culture plate (manufactured by Becton, Dickinson and Company) at a cell density of $3.75 \times 10^4$ cells/$cm^2$.

2-4 Culturing Method

After the cells were seeded as described in the items 2-1 and 2-2, the cells were cultured in an incubator at 37° C. and 5% $CO_2$. After culturing for 24 hours, the culture medium was changed once a day or once every two days. As the culture medium, there was used a medium which was obtained adding a human recombinant HGF (50 ng/ml) and an epidermal growth factor (EGF) (10 ng/ml) to a DMEM and nutrient mixture F-12 Ham medium (DMEM/F12 1:1 mixture) mixed with 10% fetal bovine serum (FBS), human γ-insulin (1.0 μg/ml), nicotinamide (10 mmol/l), dexamethasone ($1 \times 10^{-7}$ mol/l), and L-glutamine (2 mmol/l).

3. Gene Expression Analyses

Gene expressions of a cytochrome P450 (CYP), which is typical drug-metabolizing enzymes of a liver, and albumin were evaluated by carrying out real-time polymerase chain reaction after RNAs were collected from cells cultured for a given number of days to synthesize cDNAs.

4. Experimental Results (Results of Gene Expression Analyses)

Table 1 shows gene expression levels of albumin, CYP3A4, and CYP2C9 in Example 01 and Comparative Examples 01 and 02 after culturing for 21 days. In the table, relative values are shown as the gene expression levels assuming that the value of Example 02 is 1. In addition, the CYP3A4 and the CYP2C9 are examples of metabolic enzymes existing in the liver and each represent a molecular species name of a cytochrome P450 enzyme. CYPs play an important role of protecting living bodies from heterogeneities or foreign materials including various chemical agents (including drugs), environmental pollutants, and organic solvents.

Example 01 shows a significantly higher expression level than Comparative Examples 01 and 02 in any of the albumin, CYP3A3, and CYP2C9.

The experimental conditions, such as the number of cells and the mixing ratio, except for the case where different two types of cells are mixed and cultured, are not limited to the above-described conditions. Surface coating is not limited to the above, as long as cells can be adhered.

TABLE 1

|  | Albumin | CYP3A4 | CYP2C9 |
|---|---|---|---|
| Example 01 | 105.1 | 458.0 | 51.8 |
| Comparative Example 01 | 80.9 | 183.2 | 41.4 |
| Comparative Example 02 | 1 | 1 | 1 |

<Results of Culture of Liver Cells Derived from Various Donors in a Plate Including Mirco Spaces>

1. Cell Seeding

In an example, human fetal liver cells obtained from six donor livers were used. Specifically, there were used the human fetal liver cells derived from six donors, which include three types of cells: hepatic stem cells, liver precursor cells, and adult liver cells. In a comparative example, human fetal liver cells obtained from a single donor. In both the example and the comparative example, the cells were seeded in 24-well type culture chambers coated with a type-IV collagen and including micro spaces having dimensions of a=100 μM and c=50 μm as shown in FIGS. 3 and 4 at a cell density of $3.75 \times 10^4$ cells/cm².

2. Culture

Culture was carried out in an incubator at 37° C. and 5% $CO_2$. After culturing for 24 hours, the culture medium was changed once a day or once every two days. As the culture medium, there was used a medium which was obtained adding a human recombinant HGF (50 ng/ml) and an epidermal growth factor (EGF) (10 ng/ml) to a DMEM and nutrient mixture F-12 Ham medium (DMEM/F12 1:1 mixture) mixed with 10% fetal bovine serum (FBS), human γ-insulin (1.0 μg/ml), nicotinamide (10 mmol/l), dexamethasone ($1 \times 10^{-7}$ mol/l), and L-glutamine (2 mmol/l).

3. Analyses 3-1. Morphology Observation

Observations were carried out using an inverted microscope on the 1st, 4th, 7th, 14th, 21st, and 35th day of culture.

3-2. Gene Expressions of a Cytochrome P450 (CYP) and Albumin, and Protein Expression of CYP3A4

Gene expressions of a cytochrome P450 (CYP) which is typical drug-metabolizing enzymes of a liver and albumin were evaluated by carrying out real-time polymerase chain reaction after RNAs were collected from cells cultured for a given number of days to synthesize cDNAs. Protein expression was analyzed using an immunostaining procedure.

3-3. Glycogen Storage Capability

Differentiation capability (glycogen storage capability) in human fetal liver cells was measured by PAS staining.

4. Results 4-1. Results of Morphology Observation

Figure 12:
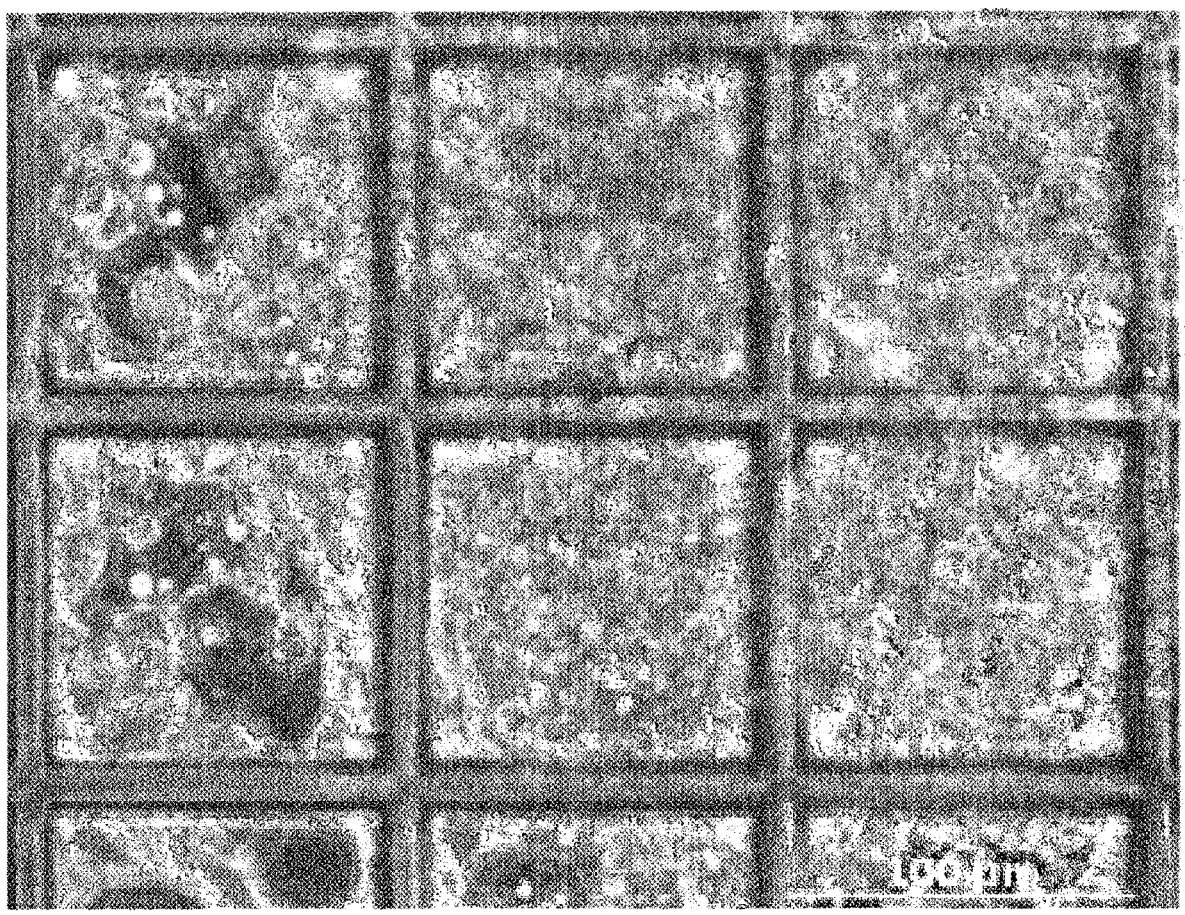
FIG. 12 is a photograph showing a result of morphology observation on the 14th day of culture of a comparative example.

Cells were adhered to the bottom surfaces of films at first, and was then gradually extended to other micro spaces (micro cavity) with the lapse of culture time and formed cell aggregates in the micro spaces. The morphology was similar to that of the comparative example described below. Accordingly, it turns out that cells of various donors can form an aggregate in the same manner as cells of one donor. FIGS. 11A to 11F are photographs showing results of morphology observations of the example. FIG. 12 is a photograph showing a result of morphology observation on the 14th day of culture of the comparative example;

4-2. Results of Gene Expressions of the Cytochrome P450 (CYP) and the Albumin, and the Protein Expression of CYP3A4

Figure 13:
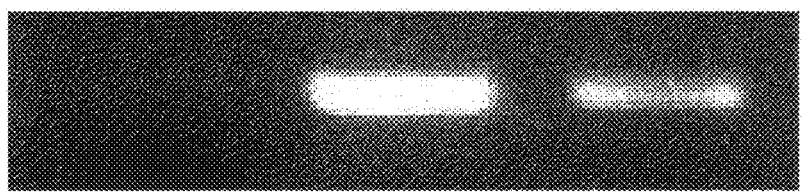
FIG. 13 is a photograph showing measurement results of primary drug-metabolizing enzyme and albumin secretory capability of an example.
Figure 13:
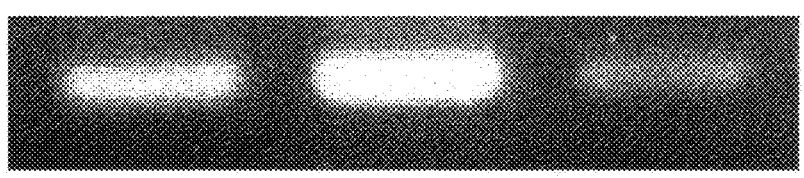
Figure 13:
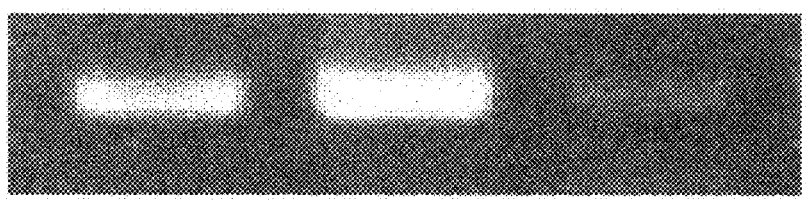
Figure 13:
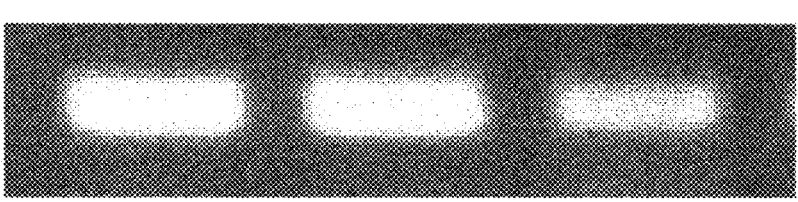
Figure 13:
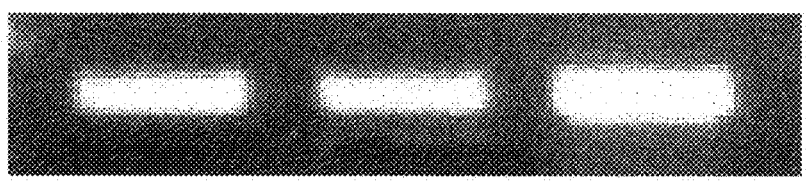
Figure 13:
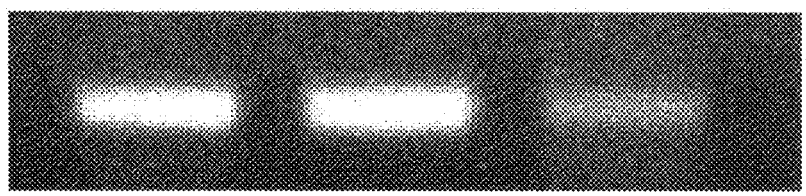
Figure 13:
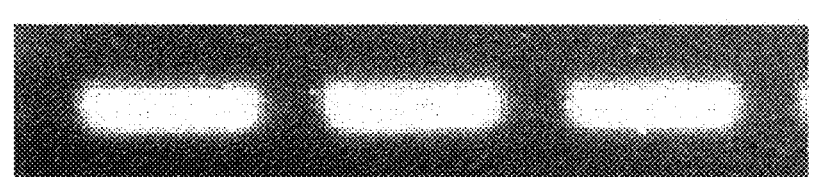

Primary drug-metabolizing enzymes CYP3A4, 2C19, 2C9, 1A2, and 2D6, and albumin secretory capability were measured. In the results, these CYP genes were expressed on the 7th day of culture, and the albumin and these CYP genes were expressed on the 21st day of culture. Even with the lapse of time, these functions were maintained. FIG. 13 is a photograph showing the measurement results. FIG. 13 shows the result obtained on the 7th day of culture on the left side, the result obtained on the 21st day of culture in the center, and the result obtained on the 35th day of culture on the right side.

Figure 14:
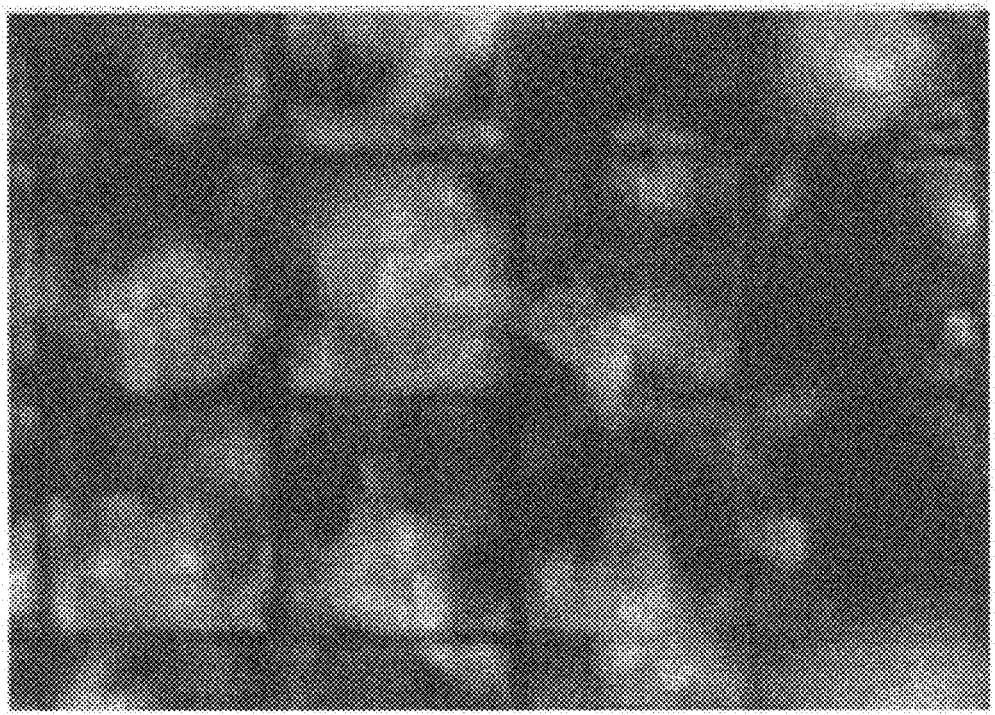
FIG. 14 is a photograph showing an immunostaining result (culture for 28 days) of an example.

In the immunostaining procedure, expressions of CYP3A4 (red) were confirmed in almost all the micro spaces (FIG. 14).

Figure 15:
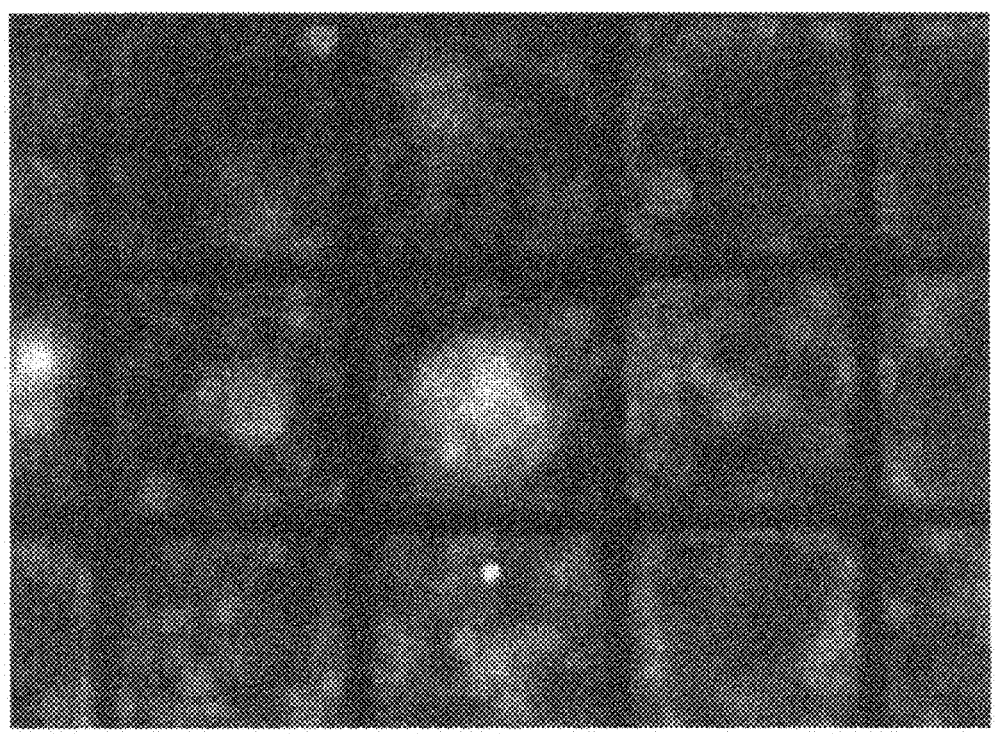
FIG. 15 is a photograph showing an immunostaining result (culture for 30 days) of a comparative example.

This stained image was similar to that of CYP3A4 of the comparative example described below (FIG. 15). Accordingly, it turns out that it is possible to culture cells of various donors while maintaining liver functions, in the same manner as cells of one donor.

4-3. Results of Glycogen Storage Capability

The differentiation capability (glycogen storage capability) in human fetal liver cells was studied. In the results, the glycogen storage capability was confirmed in the human fetal liver cells. Further, more than half of these cells were strongly PAS-positive on the 21st day of culture.

The results of 4-1 to 4-3 show that it is possible to culture liver cells of various donors while maintaining liver functions in a state where liver cells of various donors are adhered to micro spaces.

Note that the present invention is not limited to above-described embodiments. The elements of the embodiments can be modified, added, or converted to the contents that can be easily thought of by those skilled in the art within the scope of the present invention.

REFERENCE SIGNS LIST 10, 20 CELL CULTURE CHAMBER
11 MICROCHAMBER
12 SIDE WALL
13 OPENING
23 SPOT
24 SIDE WALL OF SPOT
30 CELL CULTURE KIT
31 CELL CULTURE CHAMBER

32 CULTURE PLATE
33 MICROCHAMBER
34 CULTURE DISH
D1, D2, D3 CELL

The invention claimed is:

1. A method of manufacturing a cell culture kit, comprising:
obtaining liver cells from at least two different human donors;
seeding the liver cells in a plurality of micro spaces contained in each of a plurality of chambers in a cell culture plate, with liver cells from only one of the different human donors seeded in at least one of the micro spaces, and liver cells from at least two of the different human donors seeded in at least one of the micro spaces separate from a micro space containing liver cells from only one of the different human donors, and the at least one micro space containing cells from only one of the different human donors is adjacent to the micro space that contains cells from the at least two of the different human donors;
adhering the seeded cells to the plurality of micro spaces; and
culturing the seeded liver cells within the micro spaces in a culture medium,
wherein the plurality of micro spaces each have a bottom area of 0.01 mm² to 0.1 mm², a depth of 25 μm to 150 μm, and walls partitioning the micro spaces with each side wall having a width in the range of 3 μm to 15 μm,
wherein an inorganic hydrophilic membrane is uniformly formed on the surface of the chambers, and
wherein an organic film made of extracellular matrix suitable for cultured cells is disposed on the inorganic hydrophilic membrane, and the seeded liver cells adhere to the film.

2. The method of claim 1, wherein liver cells from at least two of the different human donors are seeded in at least one micro space adjacent to the micro space that comprises the liver cells from the at least two of the different human donors.

3. The method of claim 1, wherein the cells comprise a liver stem cell.

4. The method of claim 1, wherein the cells comprise at least one selected from the group consisting of a cell differentiated from an embryonic stem (ES) cell and a cell differentiated from an induced pluripotent stem (iPS)-cell.

5. The method of claim 1, wherein the cells aggregate and form a three-dimensional structure during culturing.

6. The method of claim 1, wherein the cells are seeded in the plurality of micro spaces at a density of $1 \times 10^2$ to $1 \times 10^6$ cells/cm².

7. The method of claim 1, wherein the cells form a cell aggregate in each of the plurality of micro spaces.

8. The method of claim 7, wherein the cell aggregate has a diameter of 30 to 200 μm.

9. The method of claim 1, wherein the cells comprise a liver precursor cell.

10. The method of claim 1, wherein the liver cells are isolated from hepatic tissues of the at least two different human donors.

11. The method of claim 1, wherein the culture medium covers the plurality of micro spaces.

12. The method of claim 1, further comprising before seeding the cells, obtaining the cells from more than two of the different human donors.

13. The method of claim 1, wherein each chamber further comprises a plurality of spots, the plurality of spots are regions containing the plurality of micro spaces, and the different spots containing the micro spaces are partitioned from each other by a side wall.

* * * * *

UNITED STATES PATENT AND TRADEMARK OFFICE
CERTIFICATE OF CORRECTION

PATENT NO. : 10,836,996 B2  
APPLICATION NO. : 15/010468  
DATED : November 17, 2020  
INVENTOR(S) : Yoko Itchoda et al.

Page 1 of 1

It is certified that error appears in the above-identified patent and that said Letters Patent is hereby corrected as shown below:

On the Title Page

In Column 2, item (56), Other Publications, Line 8, delete "Olsaysky" and insert -- Olsavsky --, therefor.

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*